(12) United States Patent
Torossian

(10) Patent No.: US 6,503,512 B1
(45) Date of Patent: Jan. 7, 2003

(54) ANTI-AIDS IMMUNOMODULATOR COMPLEX

(76) Inventor: Fernand Narbey Torossian, 10, rue Noel-Ballay, F-31400 Toulouse (FR)

(*) Notice: Subject to any disclaimer, the term of this patent is extended or adjusted under 35 U.S.C. 154(b) by 0 days.

(21) Appl. No.: 08/347,322

(22) PCT Filed: Feb. 18, 1994

(86) PCT No.: PCT/FR94/00184
§ 371 (c)(1),
(2), (4) Date: Jan. 30, 1995

(87) PCT Pub. No.: WO94/22462
PCT Pub. Date: Oct. 13, 1994

(30) Foreign Application Priority Data

Mar. 31, 1993 (FR) .............................. 93 03879

(51) Int. Cl.⁷ ............................................ A61K 39/385
(52) U.S. Cl. ................ 424/197.11; 424/203.1; 424/234.1; 424/282.1
(58) Field of Search .................... 424/203.1, 234.1, 424/282.1, 193.1, 197.11

(56) References Cited

U.S. PATENT DOCUMENTS 4,297,272 A * 10/1981 D'Hinterland et al.
4,349,540 A * 9/1982 D'Hinterland et al.

FOREIGN PATENT DOCUMENTS

| CA | 1103155 | * | 6/1981 |
| CA | 1139302 | * | 1/1983 |
| CA | 1181703 | * | 1/1985 |
| EP | 0 013 851 | | 8/1980 |
| EP | 0 031 285 | | 7/1981 |
| FR | 2388563 | | 11/1978 |
| GB | 1603340 | * | 11/1981 |

OTHER PUBLICATIONS

Fahey et al., *Clin. Exp. Immunol.* 88:1–5, 1992.*
Fox, J.L., *Bio/Technology* 12:128, Feb. 1994.*
Haynes et al., *Ann. Med.* 28: 39–41, 1996.*

* cited by examiner

*Primary Examiner*—James Housel
*Assistant Examiner*—Zachariah Lucas
(74) *Attorney, Agent, or Firm*—Young & Thompson

(57) ABSTRACT

An immunomodulator complex for inhibiting intracellular replication of HIV retrovirus comprises cellular membrane fractions from at least one bacterial microorganism, and ribosomal RNA of that microorganism. The ribosomal RNA is covalently coupled to a glycoprotein amino acid sequence of type III collagen.

7 Claims, No Drawings

ANTI-AIDS IMMUNOMODULATOR COMPLEX

The present invention relates to an anti-AIDS therapeutic vaccinal complex, which has vaccination effectiveness connected to the presence of non-specific antigens.

It is well known in bacteriology that the antigens at the surface of walls, membranes or capsules (combined or liberated in soluble form in culture medium) are of glycoproteic, polypeptidic or polysaccharidic nature.

Recent vaccines have been widely publicized, associating with RNA (ribosomal origin) of such proteoglycanic or polysaccharidal membranal substances, extracts of pathogenic germs.

These vaccines use specific antigens corresponding to specifically predetermined microbial diseases.

However, the antigenic power is essentially connected to the RNA level (of the ribosomes in particular) of the microbial cells, among others. The ICC (immunologically competent cells) use directly the RNA as active transporters.

To build our new vaccinal complex, instead of using a serotypical bacterial antigen, we have coupled (by preferably covalent bonds) RNA (preferably of ribosomal origin) to a sequence of amino acids of glycoprotidic nature, present in collagen of type III (in humans, collagen represents approximately one-third of the proteins of the organism; type III has been selected for its amino acid sequence and because it is present essentially in the skin and the vascular walls).

Moreover, RNA is already used in the preparation of acellular vaccines (cf. *Infect. and Immunity*, 1, 574–82, 1970). This RNA is stabilized by associative factors.

In our complex, we use as stabilizer cellular membrane fractions from the same germs as those which have served for the elaboration of ribosomal RNA. These membranal fractions contain all the peptidalglycanic substances and are known moreover as immunal adjuvants.

Contrary to convention, it is not necessary to have the same membranal fractions (glucopolysaccharidal or proteoglycanic) from the same microbial germs as those which serve to supply RNA by extraction of their ribosomes.

Constituents of the Vaccinal Complex According to the Invention

A—Useful RNA of ribosomal origin can be extracted from the following strains, this list not being limiting:
 Klebsiella pneumoniae
 Streptococcus (*pneumonia and pyogens*)
 Staphylococcus aureus
 Serratia marcescens
 Escherichia coli
 Salmonella typhimurium
 Corynebacterium (*granulosum, parvum, acnes*)
 Mycobacterium (*tuberculosis, smegmatis, chelonei*)
 Hemophilus influenzae
 Pneumocoque type II
 Rothia dento cariosus
 Bacterium coli
 Shigella dysentariae
 Enterococcus
 Nocardia (*asteroides, brasiliensis, rhodocrans, opaca, rubra*)
 Bacillus of Calmette and Guerin The mean molecular weights of these RNAs are between 5,104 and 108 Daltons.

Many industrial processes exist for the preparation of RNA; there will be cited as example the process for the extraction of RNA described in *Infect. and Immunity*, 1, 574–82, 1970: the bacteria are agitated and then subjected to fractional precipitation, the ribosomal proteins are solubilized, the precipitated RNA is treated with Pronase and finally, purified by ion exchange chromatography.

If RNA is obtained by enzymatic means, the final purification can be effected by molecular sieve chromatography. See particularly on this subject:
 C. EHRESMAN (1972)—Biochimie, 54, 901
 H. KAGAWA (1972)—J. Biochem., (1972), 827
 M. SANTER (1973)—J. Bact., 116, 1304
 NOMURA (1974)—Ribosomes—Ed. Cold Spring Harbor Laboratory.

B—The membranal fractions of usable bacterial cells can be extracted from the following strains, the given list not being limitative:
 1 —for capsular polysaccharides
  Klebsiella pneumoniae
  Streptococcus pneumoniae
  Hemophilus influenzae
  Escherichia coli
Klebsiella pneumoniae
 C. ERBING, L. KENNE, B. LINBERG, J. LONNGREN (1976)—"Structural studies of the capsular polysaccharide of Klebsiella pneumoniae type I (*Carbohydr. Res.*, 50 (1976) 115–20).
 W. NIMMICH (1968)—"Zur Isolierung und qualitativen Bausteianalyse der K. Angigen von. Klebsiellen" (*Med. Mikrobio. und Immunol.*, 154 117, 131).
 C. RICHARD (1973)—"Etude antigenique et biochimique de 500 souches de Klebsiella" (*Ann. Biol. Clin.*, 1973).
Streptococcus pneumoniae
 F. KAUFFMANN and E. LUND (1954) (*Int. Bull. Bact. Nomencl.* 4, 125–28).
 FELTON and OTTINGER (J. of Bacteriology, 1942, 43, 94, 105)
 M. COLIN, M. D. MAC LEOD and colleagues—"Prevention of *pneumococcal pneumoniae* by immunization with specific capsular polysaccharides" (*J. Exp. Med.*, 1945, 82, 445–65).
 A. R. DOCHEZ and O. T. AVERY—"The elaboration of specific soluble substance by Pneumococcus during growth" (1971) (*J. Exp. Med.* 16, 477–93).
 WEST PHAL and LUDERITZ (1952) (Z. Naturf. 7B, 148).
 C. P. J. GLAUDEMANS and H.P. TREFFERS, "An improved preparation of the capsular polysaccharide from *Diplococcus pneumoniae* (*Carbohydr. Res.* 1967, 4, 181–84).
Hemophilus Influenzae (Capsular Polysaccharide of Poly-Ribosphorphate Type)
 P. ANDERSON and colleagues (1972)—"Immunization of humans with polyribosephosphate, the capsular antigen of *Hemophilus influenzae* type B" (*J. of Clin. Invest.*, Vol. 51, 1972, 39–44).
 P. ANDERSON and colleagues (1977)—"Isolation of the capsular polysaccharide from supernatant of Hemophilus influenzae type B" (Infect. and Immun., 1977, 15(2), 472–77).
*Escherichia coli* (Capsular Polysaccharides)
 LUDERITZ and colleagues (1977)—"Somatic and capsular antigens of gram-negative bacteria" (Compr. Biochem. 26 A, 105–228).

2—for membranal lipopolysaccharides (LPS) Corynebacterium (avidum, bovis, diphteriae, enzymicum, equi, fascians, flaccum, faciens, flavidum, fusiforme, granulosum, helvolum, hypertrophicans, insidiosum, liquefaciens, parvum, paurometabolum, pyogenes, tumescens, xerosis) and the gram negative:

Klebsiella (pneumoniae and rhinoscleromatis)
Salmonella typhimurium
Serratia (marcescens, corralina, indica, polymuthica, kiluea)
Neisseria meningitidis
Escherichia coli C. ERBIN and colleagues (1977)—"Structural studies on the Klebsiella LPS" (Carbohydr. Res., 56, 377–81).

C. B. CASTOR and colleagues (1971)—"Characteristics of a highly purified pyrogenic LPS of Klebsiella pneumoniae (J. of Pharm. Sci., 60, (10), 1578–80).

K. FUKUSHI (1964)—"Extraction and purification of endotoxin from Enterobacteriaceae: a comparison of selected methods and sources" (J. of Bacteriol. 87, (2), 391–400).

G. A. LIMJUCO—"Studies on the chemical composition of LPS from Neisseria meningitidis group B" (J. of Gen. Microbiol. 1978, 104, 187–91).

G. A. ADAMS (1967)—"Extraction of LPS from gram-negative bacteria with DMSO" (Canad. J. Biochem., 45, 422–26).

K. G. JOHNSON (1976)—"Improved techniques for the preparation of bacterial LPS" (Canad. J. Microbiol. (22), 29–34).

Y. B. KIM and colleagues (1967)—"Biologically active endotoxins from Salmonella mutants (J. of Bacteriol., 94, (5), 1320–26).

3—For Membranal Proteins

Escherichia coli
Serratia marcescens
Streptococcus pyogenes
Salmonella typhimurium
Escherichia coli S. F. STIRM and colleagues (1967)—"Episome, carried surface antigen K88 of Escherichia coli (J. of Bacteriol., 93, (2), 731–39).

S. J. BETZ and colleagues (1977)—"Chemical and biological properties of a protein rich fraction of bacterial LPS" (J. of Immunol., 119, (4), 1475–81).

Serratia marcescens

W. WOBER (1971)—"Studies on the protein moiety of endotoxin from gram-negative bacteria, characterization of the protein-moieting isolated by acetic acid hydrolysis of endotoxin of Serratia marcescens".

Streptococcus pyogenes

M. K. WITTNER (1977)—"Homologous and heterologous protection of mice with group-A Streptococcal M protein vaccine" (Infect. and Immun., 1977, 15, (1), 104–8).

Salmonella thyphimurium

N. KUUSI and colleagues (1979)—"Immunization with major outer membrane protein in experimental salmonellosis of mice" (Infect. and Immun., 1979, 25, (3), 857–62).

C. BARBER and colleagues (1972)—"The protective role of proteins from Salmonella thyphimurium in infection of mice with their natural pathogen" (Rev. Immunol., 36, 77–81).

G. DELORD (1979)—"Etude d'un antigene vaccinant contenu dans le surnageant de culture de Salmonella thyphimurium, souche M-206", Medical Thesis at Lyon, No. 428, 1979.

G. W. GOODMAN (1979)—"Characterization of the chemical and physical properties of a novel B-lymphocyte activator endotoxin protein" (Infect. and Immun., 1979, 24 (3), 685–96).

4—For Teichoic and Lipoteichoic Acids

Streptococcus, staphylococcus, and lactobacillus (the surface of the Gram-positive bacteria is made of teichoic acid, which is a polymer of glycerol, linked by phosphodiester linkages).

The following articles describe the processes of production:

M. M. BURGER (1966)—"Teichoic acids: antigenic determinants, chain separation and their location in the cell wall" (Microbioloqv 56, 910–17).

K. W. KNOX (1973)—"Immunological properties of teichoic acids" (Bacteriol. Reviews, 37, 21, 215–57).

G. A. MILLER (1976)—"Effects of streptococcal lipoteichoic acid on host response in mice" (Infect. and Immun., 1976, 13, (5), 1408–17).

A. J. WICKEN and colleagues (1975)—"Lipoteichoic acids: a new class of bacterial antigens" (Science, 187, 1161–67).

Different Possible Dosages

RNA

*FISKE and SUBBAROW—"Dosage du phosphore. Chromatographie HPLC sur colonne echangeuse d'ions pour le controle qualitatif" (J. Biol. Chem. (1926), 66, 375).

Proteins

*LOWRY (J. Biol. Chem. (1951), 193, 265–75).

Hexoses

*T. A. SCOTT—"Dosage colorimetr. a l'anthrone" (Anal. Chem. (1953), 25, 1956–61).

Hexosamines

*L. A. ELSON (Biochem. J. (1953), 27, 1824–28).

Lipopolysaccharides

*J. JANDA and E. WORK (Febs Letters, 1971, 16(4), 343–45).

C—Other adiuvant factors of immunity, in addition to membranal fractions, are of collagen type III
of sodium chloride The Type III collagen used is characterized by:

a—amino acid sequences similar to the following list (the concentrations are expressed in g/kg):

| aspartic acid | AA | 51.5 |
|---|---|---|
| hydroxyproline | HP | 107.0 |
| threonine | TH | 16.1 |
| serine | SE | 27.8 |
| glutamic acid | GA | 95.9 |
| proline | PR | 124.0 |
| glycine | GL | 149.0 |
| alanine | AL | 87.9 |
| valine | VA | 23.3 |
| methionine | ME | 7.5 |
| isoleucine | IL | 14.4 |
| leucine | LE | 27.8 |
| tyrosine | TY | 6.7 |
| phenylalanine | PA | 14.4 |
| lysine | LY | 28.6 |
| histidine | HI | 5.5 |
| arginine | AR | 73.0 | b—analysis type as follows:

| color | yellowish white |
|---|---|
| apparent density | 250 g/l |
| humidity | 6% |
| pH of a 10% solution | 6.9 |
| Engler viscosity at 40° C. (17.75% solution) | 2.5 |
| fatty material content | 0.9% |
| ash content | 2.2% |
| Fe + Cu + Ca content | 462 mg/kg |
| heavy metals | not determinable by emission arc spectography |
| elemental analysis | C   46.80% |
|  | H    7.10% |
|  | N   14.96% |

The composition of the vaccinal complex according to the invention, associating RNA or ribosomal RNA fragments, membranal fractions (for example proteoglycanes of Klebsiella pneumoniae) and of type III collagen, completed by sodium chloride and an anti-inflammatory, permit, by administration of low doses giving rise to no toxicity, obtaining a high level of protection and of cure.

The preferred formulation is the injectable form of the composition described above, but it is possible to use other forms and/or other supports or additives compatible with medical usage.

Mechanism of the Action of the Vaccinal Complex

The therapeutic vaccinal complex which has been described has the characteristics of a lymphokine which, adhering to the macrophages, inhibits the intra-cellular increase of the virus.

Since 1974–75 (A. S. and G. P. YOUMANS), it has been considered that the inhibitory effect of the immune response to RNA was produced by different inhibitors.

This has lead us to conceive the vaccinal complex, according to the invention, which gives rise to the same inhibition of the replication of the HIV retrovirus.

YOUMANS worked on a single bacterial strain (*Mycobacterium tuberculosis*), whose "parasitism" is solely intracellular.

VENNEMAN and colleagues believe, since 1972, that the true antigen could be associated with RNA, whose role would be that of an adjuvant. They vaccinated mice with ribosomal RNA, extracted with phenol at 65° from ribosomes of the strain *Salmonella typhimurium*. Thirty days after this vaccination, they noted that the animals are better protected than by live vaccinal strain (attenuated).

It is above all believed that the level of protection is a function of the quantity of RNA injected.

It is now known that ribosomal RNA extract of *Streptococcus pneumoniae* produces a protection of humoral nature and that ribosomal RNA extract of *Klebsiella pneumoniae* induces a natural cellular protection.

Preliminary experiments, by DUSSOURD d'HINTERLAND, FONTANGES and colleagues (Division of Microbiology of the Research Center of the Military Health Service of Lyon, France), have thus demonstrated that this mixture, injected in vivo in mice and guinea pigs, has an action on the alveolar macrophages.

This "transitory" effect occurs when dosing the acid phosphatase, and the direct hemolyses regions when in contact with the splenic cells of mice.

Immunological studies carried out by DUSSORD d'HINTERLAND from ribosomal vaccines, induce in O. F. female mice the production of specific antibodies when they are administered to the animal in the presence of FREUND (incomplete) adjuvant or membranal protolycanes of Klebsiella.

The treatment with our vaccinal complex is as to itself followed by a cellular and humoral immunostimulant effect, with nonspecific action, but significant, on HIV. This action can be likened to the production of a "V.N.F." (Virus Necrosis Factor), because it is the organism of the patient himself which is urged to reject the infected cells (antigen P24 being, for this reason, reduced to zero in almost all cases).

The therapeutic technique of S. ROSENBERG is not identical to ours, although it is rather close. He localized on human DNA the gene which produces the "T.N.F." (Tumor Necrosis Factor). After having cloned on *Escherichia coli* and reproduced, he introduced it, with the aid of a vector virus, into lymphocytes T (Tueurs) which are found in tumors.

Our therapeutic mechanism permits producing a natural cloning thanks to the RNA (non-specific ribosomal bacteria) opsonized by the improved adjuvant (combination of membranal proteolycanes, of type III collagen, of sodium chloride).

This cloning induces a vaccination against idiotypes of the anti-HIV antibodies, as well as the production of antibodies against the site of bonding of the virus to the molecule CD4, in particular. To increase or inhibit the auto-immune anti-CD4 reaction (which contributes to lymphopeny CF4), it is necessary to use, during treatments with the vaccinal complex, corticoids (Betamethazone type) in the form of disodium phosphate, at a dosage of 20 to 60 mg, by the IV or IM route.

This action is also accompanied by a production of endogenous interferon, as well as an activation of the N. K. cells.

The object of our immunomodulatory vaccinal complex is therefore to induce an immune response having for its effect to prevent or at least to reduce (to a possible auto defense threshold), the proliferation of an infectious agent, viral in this case, introduced into the organism.

Our therapeutic novelty consists among other things in moderating or suppressing the existence of "suppressive cellules" exerting a pro-infectious action.

Our treatment gives rise to an anti-AIDS reaction by a cellular and/or humoral defense response.

In conclusion, our therapeutic compound acts by directed evolution producing RNA molecules, which, binding to viral proteins, block the infection by AIDS retrovirus.

Techniques for Administration of the Vaccinal Complex

The vaccinal complex can be administered by oral route, but the preferred method is by the parenteral route:
either by direct intravenous direction
or by slow perfusion
or again by subcutaneous injection.

This various techniques have been carried out experimentally with success.

The daily dosages and their frequency depend greatly on the condition of the patient. An overdose has no risk, given the very low toxicity of the complex.

By intravenous route, can be used frequencies of one week per month, each day of the week of treatment comprising a slow perfusion of 500 ml of a solution containing:

0.9% sodium chloride
40 μg of membranal saccharidic fractions (proteoglycanes of Klebsiella pneumoniae)
22 μg (ribosomal) RNA of:

| Diplococcus pneumoniae | 7 μg |
| Streptococcus pyogens (A 12) | 7 μg |
| Klebsiella pneumoniae | 7 μg |
| Hemophilus influenzae | 1 μg |

10 μg of type III collagen described above
8 mg of disodium phosphate of Betamethazone (namely 2 ml of injectable solution)

This treatment by slow intravenous perfusion can be followed by a treatment by subcutaneous injections of the patients which can be carried out on an ambulatory basis, each injection containing 40 μg of membranal saccharidic fractions (proteoglycanes of *Klebsiella pneumoniae*)
22 μg (ribosomal) RNA of:

| Diplococcus pneumoniae | 7 μg |
| Streptococcus pyogen (A 12) | 7 μg |
| Klebsiella pneumoniae | 7 μg |
| Hemophilus influenzae | 1 μg |

10 μg of type III collagen described above
0.5 ml of 0.9% sodium chloride
4 mg of disodium phosphate of Betamethazone (namely 1 ml of injectable solution).

This treatment can be performed for several months, until the seropositivity is completely negated (that is to say AgP24 =0)

The following non-limiting examples are given to illustrate the concrete results of our therapeutic vaccinal complex.

EXAMPLE 1

Mr. J. A. . . . , 65 years old, hemophilic, was infected during a transfusion received eight years previously. AIDS and hepatitis (Group IV C2). A major deterioration took place in September, 1991. Hospitalized, he suffered from asthenia, loss of weight, intestinal troubles, rhino-sinusitis, etc. . . . Treatment with AZT failed.

September, 1992—beginning of treatment with our vaccinal complex: series of intravenous perfusions, followed, in December, 1992, by a series of subcutaneous injections.

At present, there is observed:
a good general condition
weight gain
seronegativity as to AgP24.

EXAMPLE 2

Mme A. A. . . . , 59 years old, wife of the preceding patient, underwent a serious deterioration in May, 1992 with asthenia and weight loss (Group IV A).

September, 1992—beginning of treatment with our vaccinal complex: intravenous perfusion series, followed, in December, 1992, by a series of subcutaneous injections.

At present, there is noted:
an excellent general condition regaining initial weight
seronegativity as to AgP24

EXAMPLE 3

Mr. E. C. . . . , 30 years old, was contaminated by a sexual contact six years previously. AIDS was diagnosed in 1988 (Group IV Cl). In 1992, the patent suffered asthenia, then the beginning of pneumocytosis (treatment with AZT+Bactrim Forte).

September, 1992—beginning of treatment with our vaccinal complex: series of subcutaneous injections only, with discontinuance of all other therapy.

At present, there is noted:
an excellent general condition (having permitted an extension of professional activity)
seronegativity as to AgP24;

These treatments by the vaccinal complex have been practiced on various patients at their express request and by reason of the obvious ineffectiveness of their previous treatments.

What is claimed is:

1. Immunomodulator complex comprising cellular membrane fractions from at least one bacterial microorganism selected from the group consisting of *Klebsiella pneumoniae, Klebsiella rhinoscleromatis, Streptococcus pneumoniae, Streptococcus pyogenes, Streptococcus aureus, Haemophilus influenzae, Diplococcus pneumoniae, Escherichia coli*, Corynebacterium, *Salmonella typhimurium*, Serratia, *Neisseria meningitidis*, and Lactobacillus, and ribosomal RNA of said at least one bacterial microorganism, said ribosomal RNA being coupled covalently to a type III collagen glycoprotein.

2. The immunomodulator complex according to claim 1, wherein said RNA has a mean molecular weight between 108 and 5,104 Daltons.

3. The immunomodulator complex according to claim 1, prepared in dosage form for administration by perfusion, and further comprising sodium chloride.

4. The immunomodulator complex according to claim 1, prepared in dosage form for administration by intravenous injection, and further comprising sodium chloride.

5. The immunomodulator complex according to claim 1, prepared in dosage form for administration subcutaneously, and further comprising sodium chloride.

6. The immunomodulator complex according to claim 1, prepared in dosage form for administration as a transdermal device, and further comprising sodium chloride.

7. The immunomodulator complex according to claim 1, wherein said cellular membrane fractions are glyco-peptides and/or lipopolysaccharides.

* * * * *